(12) United States Patent
Hah

(10) Patent No.: US 11,426,146 B2
(45) Date of Patent: Aug. 30, 2022

(54) ULTRASOUND IMAGING APPARATUS AND CONTROL METHOD THEREOF

(71) Applicant: SAMSUNG MEDISON CO., LTD., Gangwon-do (KR)

(72) Inventor: Zae Gyoo Hah, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 722 days.

(21) Appl. No.: 16/126,648

(22) Filed: Sep. 10, 2018

(65) Prior Publication Data

US 2019/0076128 A1    Mar. 14, 2019

Related U.S. Application Data

(60) Provisional application No. 62/580,890, filed on Nov. 2, 2017, provisional application No. 62/555,907, filed
(Continued)

(30) Foreign Application Priority Data

Apr. 12, 2018   (KR) .................. 10-2018-0042638

(51) Int. Cl.
*A61B 8/08* (2006.01)
*A61B 8/00* (2006.01)

(52) U.S. Cl.
CPC ............ *A61B 8/5223* (2013.01); *A61B 8/08* (2013.01); *A61B 8/085* (2013.01); *A61B 8/485* (2013.01);
(Continued)

(58) Field of Classification Search
None
See application file for complete search history.

(56) References Cited

U.S. PATENT DOCUMENTS

| | | | |
|---|---|---|---|
| 2009/0149750 A1* | 6/2009 | Matsumura | A61B 5/0048 600/438 |
| 2012/0108968 A1* | 5/2012 | Freiburger | A61B 8/0825 600/443 |

(Continued)

FOREIGN PATENT DOCUMENTS

| | | |
|---|---|---|
| EP | 1 864 612 A1 | 12/2007 |
| EP | 1 980 210 A1 | 10/2008 |
| WO | 2011/033050 A1 | 3/2011 |

OTHER PUBLICATIONS

Kazutoki Kogure: "Trial of a quantitative method for evaluating hemangioma of the liver and hepatocellular carcinoma using a radio-frequency signal", Journal of Medical Ultrasonics, vol. 32, No. 4, Dec. 19, 2005, pp. 159-166.
(Continued)

*Primary Examiner* — Yi-Shan Yang
(74) *Attorney, Agent, or Firm* — Morgan, Lewis & Bockius LLP

(57) ABSTRACT

An ultrasound imaging apparatus according to an embodiment comprises an ultrasonic probe to acquire an ultrasonic signal of a target object, a display, and a controller to acquire viscoelasticity data of the target object based on the acquired ultrasonic signal, determine at least one parameter for displaying the acquired viscoelasticity data, determine a parameter space for displaying the at least one parameter, and control the display to display the determined parameter in the determined parameter space.

9 Claims, 12 Drawing Sheets

Related U.S. Application Data on Sep. 8, 2017, provisional application No. 62/555,934, filed on Sep. 8, 2017.

(52) U.S. Cl.
CPC ............... *A61B 8/54* (2013.01); *A61B 8/56* (2013.01); *A61B 8/463* (2013.01); *A61B 8/466* (2013.01); *A61B 8/469* (2013.01)

(56) References Cited

U.S. PATENT DOCUMENTS

| | | | |
|---|---|---|---|
| 2015/0305719 A1 | 10/2015 | Nenadic et al. | |
| 2016/0143621 A1* | 5/2016 | Parthasarathy | A61B 8/085 600/438 |
| 2016/0143622 A1* | 5/2016 | Xie | A61B 8/0841 600/424 |
| 2016/0302769 A1* | 10/2016 | Labyed | A61B 8/463 |
| 2017/0333004 A1* | 11/2017 | Yoshikawa | A61B 5/318 |

OTHER PUBLICATIONS

Tadashi Yamaguchi, et al: "Estimation of the scatterer distribution of the cirrhotic liver using ultrasound image", Jpn. J. Appl. Phys., vol. 37, Part 1, No. 5B, May 1, 1998, pp. 3093-3096.
Search Report issued in corresponding European Application No. 18193287.2, dated Mar. 27, 2019.
Invitation pursuant to Rule 62a(1) EPC dated Jan. 4, 2019 issued in European Patent Application No. 18193287.2.

\* cited by examiner

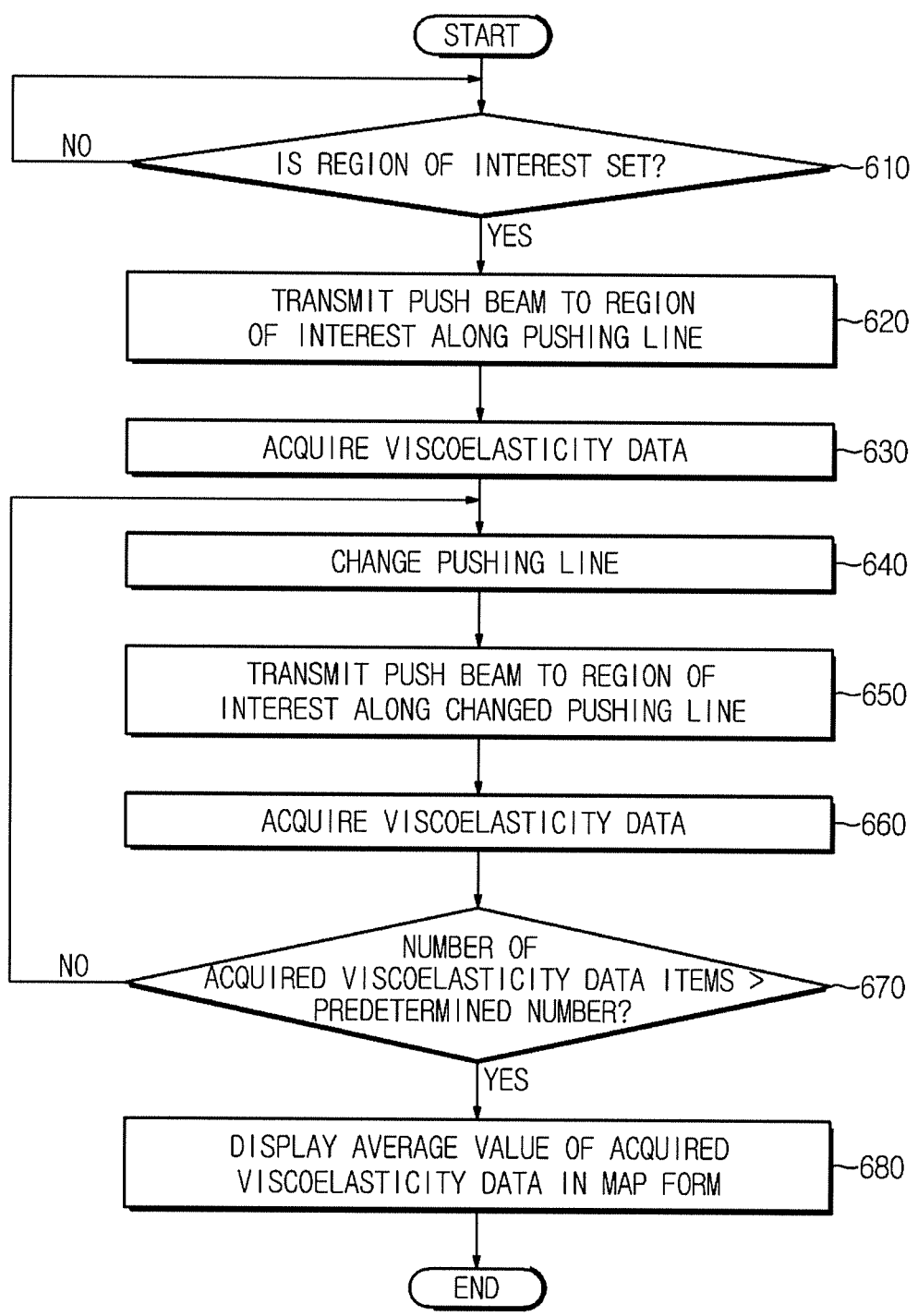

ULTRASOUND IMAGING APPARATUS AND CONTROL METHOD THEREOF

CROSS-REFERENCE TO RELATED APPLICATION(S)

This application is based on and claims priority under 35 U.S.C. § 119 to U.S. Provisional Patent Application Nos. 62/555,907 and 62/555,934, filed on Sep. 8, 2017, and 62/580,890, filed on Nov. 2, 2017 in the USPTO, and Korean Patent Application No. 10-2018-0042638, filed on Apr. 12, 2018 in the Korean Intellectual Property Office, the disclosures of which are incorporated by reference herein in their entirety.

BACKGROUND

1. Technical Field

The present disclosure relates to an ultrasound imaging apparatus and a control method thereof that generates an image of the inside of a target object using ultrasound waves.

2. Description of the Related Art

An ultrasound imaging apparatus is an apparatus that irradiates an ultrasonic signal generated from a transducer of a probe from a body surface of a target object toward a target portion in the body, and receives information of the ultrasonic signal (ultrasonic echo signal) reflected from the target object and acquires an image of a region inside the target object. Such ultrasound imaging apparatus has a function of calculating and providing clinically useful parameters from the reflected signals received through signal processing.

Ultrasound imaging devices have a higher stability than x-ray imaging devices since there is no radiation exposure and are widely used in the field of medical diagnosis because they are able to display images in real time, are cheaper than magnetic resonance imaging devices and are portable.

SUMMARY

It is an aspect of the present disclosure to provide an ultrasound imaging apparatus and a control method thereof that may provide various information necessary for diagnosing a target object using ultrasound images to a user.

Additional aspects of the present disclosure will be set forth in part in the description which follows and, in part, will be obvious from the description, or may be learned by practice of the disclosure.

In accordance with one aspect of the present disclosure, there is provided an ultrasound imaging apparatus comprising: an ultrasonic probe to acquire an ultrasonic signal of a target object; a display; and a controller to acquire viscoelasticity data of the target object based on the acquired ultrasonic signal, determine at least one parameter for displaying the acquired viscoelasticity data, determine a parameter space for displaying the at least one parameter, and control the display to display the determined parameter in the determined parameter space.

Further, the parameter space may a two-dimensional coordinate space or a three-dimensional coordinate space.

Further, the parameter for displaying the viscoelasticity data may be at least one of a shear wave speed, a shear wave attenuation coefficient, a shear wave speed dispersion, a shear wave attenuation dispersion, a viscosity, and a shear modulus.

Further, the controller may control the display to display a region corresponding to a level of liver diseases including fibrosis, steatosis and inflammation in the parameter space and display the viscoelasticity data corresponding to the level of liver diseases in the region corresponding to the level of liver diseases.

Further, the controller may determine a liver disease probability distribution space as the parameter space, and control the display to display a liver disease probability distribution and the viscoelasticity data for levels of liver disease in the determined parameter space.

In accordance with another aspect of the present disclosure, there is provided an ultrasound imaging apparatus comprising: an ultrasonic probe to acquire an ultrasonic signal of a target object; a display; and a controller to generate a predetermined number of ultrasound image frames for the target object based on the acquired ultrasonic signal, acquire viscoelasticity data for the predetermined number of ultrasound image frames, and control the display to display an average value of the acquired viscoelasticity data as numbers or in a map form.

Further, the controller may control the display to display the average value of the viscoelasticity data in a map form in a first region and display the most recently acquired viscoelasticity data in a map form in a second region.

In accordance with another aspect of the present disclosure, there is provided an ultrasound imaging apparatus comprising: an ultrasonic probe to transmit an ultrasonic signal along a pushing line to a target object; and a controller to acquire viscoelasticity data based on the ultrasonic signal transmitted by the ultrasonic probe, change the pushing line when acquiring the viscoelasticity data, control the ultrasonic probe to transmit the ultrasonic signal along the changed pushing line, and acquire the viscoelasticity data based on the ultrasonic signal for the changed pushing line.

Further, the controller may store the acquired viscoelasticity data, and display an average value of the stored viscoelasticity data as numbers or in a map form when the stored viscoelasticity data is larger than a predetermined number.

Further, the ultrasound imaging apparatus may further comprise an inputter to receive a region of interest (ROI), wherein the controller may change the position of the pushing line so that the pushing line designates another position of the ROI when the viscoelasticity data for the ROI is acquired.

In accordance with another aspect of the present disclosure, there is provided a control method of an ultrasound imaging apparatus comprising: acquiring an ultrasonic signal of a target object; acquiring viscoelasticity data of the target object based on the acquired ultrasonic signal; determining at least one parameter for displaying the acquired viscoelasticity data; determining a parameter space for displaying the at least one parameter; and displaying the determined parameter in the determined parameter space.

Further, the parameter space may be a two-dimensional coordinate space or a three-dimensional coordinate space.

Further, the parameter for displaying the viscoelasticity data may be at least one of a shear wave speed, a shear wave attenuation coefficient, a shear wave speed dispersion, a shear wave attenuation dispersion, a viscosity, and a shear modulus.

Further, the step of displaying the determined parameter in the determined parameter space may comprise displaying a region corresponding to a level of liver disease in the determined parameter space, and displaying the viscoelasticity data corresponding to the level of liver disease in the region corresponding to the level of liver disease.

Further, the step of determining the parameter space may comprise determining a liver disease probability distribution space as the parameter space, and the step of displaying the determined parameter in the determined parameter space may comprise displaying a liver disease probability distribution and the viscoelasticity data for levels of liver disease in the determined parameter space.

In accordance with another aspect of the present disclosure, there is provided a control method of an ultrasound imaging apparatus comprising: acquiring an ultrasonic signal of a target object; generating a predetermined number of ultrasound image frames for the target object based on the acquired ultrasonic signal, and acquiring viscoelasticity data for the predetermined number of ultrasound image frames; and displaying an average value of the acquired viscoelasticity data in a map form.

Further, the step of displaying the average value of the acquired viscoelasticity data in a map form may comprise displaying the average value of the viscoelasticity data in a map form in a first region, and displaying the most recently acquired viscoelasticity data in a map form in a second region.

In accordance with another aspect of the present disclosure, there is provided a control method of an ultrasound imaging apparatus comprising: transmitting an ultrasonic signal along a pushing line to a target object; acquiring viscoelasticity data based on the ultrasonic signal; changing the pushing line; and transmitting the ultrasonic signal along the changed pushing line, and acquiring the viscoelasticity data based on the ultrasonic signal for the changed pushing line.

Further, the control method may further comprise: storing the acquired viscoelasticity data, and displaying an average value of the stored viscoelasticity data in a map form when the stored viscoelasticity data is larger than a predetermined number.

Further, the control method may further comprise: receiving a region of interest (ROI), wherein the step of acquiring the viscoelasticity data based on the ultrasonic signal comprises acquiring the viscoelasticity data for the ROI, and the step of changing the pushing line comprises changing the position of the pushing line so that the pushing line designates another position of the ROI.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 11 is a flowchart illustrating a control method of an ultrasound imaging apparatus according to an embodiment.

DETAILED DESCRIPTION

Figure 1:
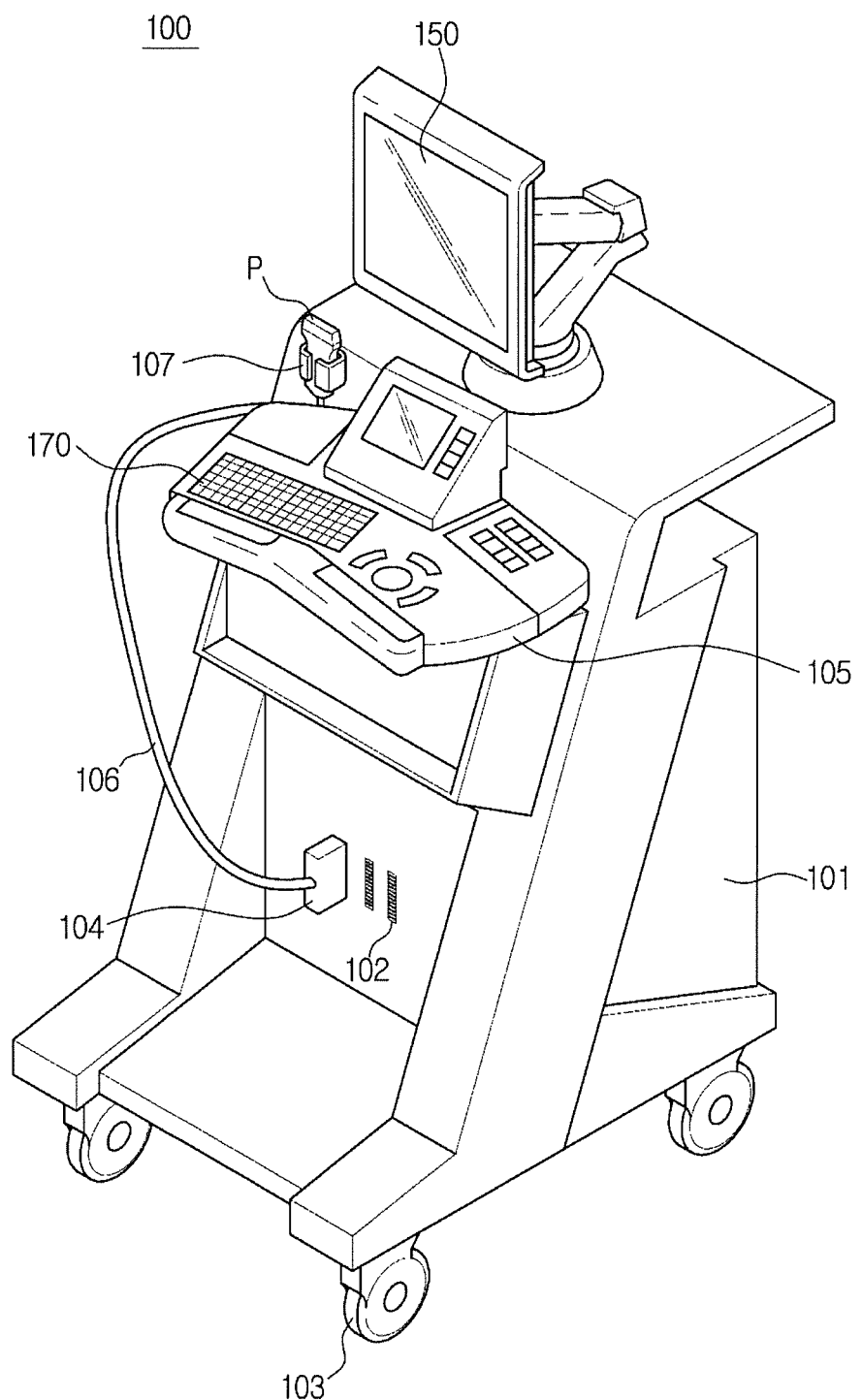
FIG. 1 is an external view of an ultrasound imaging apparatus according to an embodiment.

Like reference numerals refer to like elements throughout the specification. This specification does not describe all the elements of the embodiments, and duplicative contents between general contents or embodiments in the technical field of the present invention will be omitted. The terms 'part,' 'module,' 'member,' and 'block' used in this specification may be embodied as software or hardware, and it is also possible for a plurality of 'parts,' 'modules,' 'members,' and 'blocks' to be embodied as one component, or one 'part,' 'module,' 'member,' and 'block' to include a plurality of components according to the embodiments.

Throughout the specification, when a part is referred to as being "connected" to another part, it includes not only a direct connection but also an indirect connection, and the indirect connection includes connecting through a wireless network.

Also, when it is described that a part "includes" an element, it means that the element may further include other elements, not excluding the other elements unless specifically stated otherwise.

Throughout the specification, when it is described that a member is located "on" another member, this includes not only when a member is in contact with another member, but also when there is another member between the two members.

The terms 'first,' second,' etc. are used to distinguish one element from another element, and the elements are not limited by the above-mentioned terms.

The singular forms "a," "an," and "the" include plural referents unless the context clearly dictates otherwise.

In each step, an identification sign is used for the convenience of explanation, and the identification sign does not describe the order of each step, and each step may be performed differently from the stated order unless clearly specified in the context.

Hereinafter, the working principle and embodiments of the present disclosure will be described with reference to the accompanying drawings.

FIG. 1 is an external view of an ultrasound imaging apparatus according to an embodiment.

As shown in FIG. 1, an ultrasound imaging apparatus 100 according to an embodiment may include an ultrasonic probe P that transmits an ultrasonic wave to a target object, receives an ultrasonic echo signal from the target object and converts the received ultrasonic echo signal into an electrical signal, a main body 101, an inputter 170, and a display 150.

The ultrasonic probe P is a portion that contacts a body surface of a target object or is inserted into the body of the target object, and may transmit and receive ultrasonic waves. Specifically, the ultrasonic probe P may transmit an ultrasonic wave to the inside of the target object according to a transmission signal provided from the main body 101, receive an echo ultrasonic wave reflected from a specific portion in the target object, and transmit the echo ultrasonic wave to the main body 101.

The ultrasonic probe P may be connected to the main body 101 through a cable 106 to receive various signals required for controlling the ultrasonic probe P or to transmit an analog signal or a digital signal corresponding to the ultrasonic echo signal received by the ultrasonic probe P to the main body 101.

To this end, at least one female connector 102 may be provided at one side of the main body 101. A male connector 104 provided at one end of the cable 106 may be physically coupled to the female connector 102.

However, the embodiment of the ultrasonic probe P is not limited thereto, and the ultrasonic probe P may be wirelessly connected to the main body 101. In this case, the ultrasonic probe P may be implemented as a wireless probe to transmit and receive signals through a network formed between the ultrasonic probe P and the main body 101. In addition, a plurality of the ultrasonic probes P may be connected to the one main body 101.

A plurality of casters 103 for moving the ultrasound imaging apparatus 100 may be provided at a lower portion of the main body 101. A user may fix or move the ultrasound imaging apparatus 100 by using the plurality of casters 103. An operation panel 105 may be provided on a front surface of the main body 101. The operation panel 105 may be provided with the inputter 170 to receive the user's input, and the user may input commands for starting diagnosis, selecting a diagnosis region, selecting a diagnosis type, and selecting a mode for an ultrasound image through the inputter 170. Examples of modes for the ultrasound image include an A-mode (Amplitude mode), a B-mode (Brightness mode), a D-mode (Doppler mode), an E-mode (Elastography mode), and an M-mode (Motion mode).

The display 150 may be provided at an upper portion of the main body 101. The display 150 may be implemented using at least one of various display panels such as a liquid crystal display (LCD) panel, a light emitting diode (LED) panel, or an organic light emitting diode (OLED).

It is also possible that the display 150 is composed of two or more displays so that the respective displays may simultaneously display different images. For example, one display may display a 2D ultrasound image and the other display may display a 3D ultrasound image. Alternatively, one display may display a B-mode image and the other display may display a contrast agent image.

At least one probe holder 107 for mounting the ultrasonic probe P may be provided on an outer peripheral surface of the main body 101. Therefore, when the ultrasonic probe P is not used, the user may store the ultrasonic probe P in the probe holder 107.

As another embodiment, the ultrasound imaging apparatus 100 may be a portable ultrasound imaging apparatus that may be carried during long distance movement. At this time, the portable ultrasound imaging apparatus may not include the casters 103. Examples of portable ultrasound imaging apparatuses may include a PACS viewer, a smart phone, a laptop computer, a PDA, a tablet PC, and the like, but are not limited thereto.

A user such as a doctor may perform diagnosis of a specific disease using the ultrasound image displayed on the display 150 and the region for acquiring the ultrasound image may vary depending on the disease to be diagnosed. For example, an abdominal ultrasound image may be used to diagnose a fatty liver.

It is known that a fatty liver, which is a disease caused by fatty deposits in the liver, may develop into end stage liver disease such as hepatic cirrhosis or hepatocellular carcinoma as well as progress to steatohepatitis and hepatic fibrosis. In addition, since high prevalence rates of a fatty liver have been reported worldwide and in particular, a non-alcoholic fatty liver disease (NAFLD) is closely related to obesity and metabolic syndrome, the discovery of a fatty liver is a very important region in diagnosis using ultrasound images.

The fatty liver may be found by measuring the viscoelasticity of liver tissue. Viscoelasticity is a property of coexistence of viscosity and elasticity, which means a property accompanied by elastic deformation and viscous flow.

The viscoelastic property of the tissues in a living body, including the liver, may be measured by using an ultrasonic wave, specifically may be measured by detecting a shear wave.

When ultrasonic signals are strongly irradiated into a target object, the tissue may actually move finely, and shear waves are generated in the tissue due to the movement of the tissue. The shear waves generated by strong ultrasonic waves in the target object progress from a focus region to the periphery, and the progressing direction of the waves and the direction of vibration of the particles are vertical. The velocity of the progressing shear waves changes according to the vibrational characteristics of a medium. Accordingly, the velocity of the shear waves is a main variable for measuring the elastic properties of the medium, that is, the elastic modulus.

Therefore, the velocity of the shear waves may be measured by continuously tracking the motion of the shear waves generated in the tissue, and the elastic modulus of the tissue may be estimated from the velocity of the shear waves.

On the other hand, there may be a case where the tissue does not have pure elasticity but viscoelasticity having both elasticity and viscosity. For example, in the case of a fatty liver in which fat is accumulated in the liver, the liver has viscoelasticity having viscosity and elasticity rather than pure elasticity.

In a case where the tissue has viscoelasticity, the attenuation of a shear wave may be additionally observed. At this time, a dispersion phenomenon in which the velocity of the shear wave varies depending on the frequency may appear.

Specifically, in this case, an attenuation phenomenon occurs in which the wave energy decreases as a wave progresses in the progressing shear wave. In general, as a wave progresses, it spreads spatially, widening the wave front, and reducing the energy of the wave. In addition, the energy of the waves is reduced because a physical phenomenon occurs in which the energy of the waves is absorbed into the medium while passing through the medium. The former is attenuation by geometric spreading, and the latter is attenuation by absorption into the medium. The critical attenuation in viscoelasticity is attenuation due to absorption into the medium. To compute this, it is necessary to compensate for the component due to a geometric spreading phenomenon in the observed attenuation.

The velocity of a shear wave is not constant for each frequency component, and a speed dispersion phenomenon that varies depending on the frequency occurs. The attenuation coefficient also shows a dispersion phenomenon (attenuation dispersion).

Therefore, a system for measuring and displaying the viscoelastic property of a target object may include at least one parameter of a shear wave speed, a shear wave attenuation coefficient, a shear wave speed dispersion, a shear wave attenuation dispersion, a viscosity, and a shear modulus.

In addition, since each selected variable may deviate from the true value due to various issues such as measurement error, noise, and object motion, a method of displaying reliability together is utilized. One method of a viscoelastic system generating a shear wave in the tissue using ultrasonic waves and tracking the movement of the shear wave is described as follows. In a typical ultrasonic system, when a pushing pulse having a large F number is applied to the focal direction (z direction) in order to generate a transverse wave, the tissue near the focal point is slightly depressed and its shape is determined by the shape of the pushing pulse and the damping performance of the tissue. The shear wave generated at this time follows [Equation 1].

$$\mu \nabla^2 u_z + \rho f_z = \rho \ddot{u}_z, \quad \nabla^2 = \frac{\partial^2}{\partial x^2} + \frac{\partial^2}{\partial y^2}. \quad \text{[Equation 1]}$$

Where $\rho$ is the density of the medium, $f_z$ is the axial force, $u_z$ is the axial displacement, and $\mu$ is the shear elastic modulus.

As a method for solving [Equation 1], there is a method of performing Fourier transform in the space and time domain, as shown in [Equation 2].

$$u(x, y, t) = \quad \text{[Equation 2]}$$
$$\frac{1}{(2\pi)^{3/2}} \int \int \int \frac{F(\varepsilon, \eta, \omega)}{\varepsilon^2 + \eta^2 - (\omega^2/c^2)} e^{i(\varepsilon x + \eta y - \omega t)} d\varepsilon d\eta d\omega$$

Where $F(\varepsilon,\eta,\omega)$ is the shear push function, c is the shear velocity, and $\varepsilon$, $\eta$, and $\omega$ represent the spatial frequency and angular frequency, respectively.

In addition, if the push waveform is very short, the push wave of the shear wave may be approximated by a delta function, and assuming that the spatial distribution of the push function is a Gaussian form having the widths of $(\sigma_x, \sigma_y)$ in the lateral and elevation directions, respectively, [Equation 2] may be further simplified.

In particular, the calculation of [Equation 2] includes the singularity, so that the value of the circle of $\varepsilon^2+\eta^2=\omega^2/c^2=k^2$ is important, and is simplified to [Equation 3] below.

$$u_z(x, 0, k) = A_1 i \text{sign}(k) e^{-\frac{1}{2}k^2 \sigma_x^2} \frac{Erf\left[2\pi \sqrt{k^2 \sigma_y^2 + 2ikx}\right]}{\sqrt{k^2 \sigma_y^2 + 2ikx}} e^{ikx} \quad \text{[Equation 3]}$$

In addition, since the particle velocity is given as the time derivative of the displacement, the particle velocity may be expressed by [Equation 4].

$$v_z(x, 0, k) = i\omega u_z\left(x, 0, \frac{\omega}{c}\right). \quad \text{[Equation 4]}$$

From [Equation 3], the attenuation due to geometric spreading may be calculated as the shear wave progress. That is, the following [Equation 5] is derived.

$$|u_z(x_1, 0, \omega)| \approx |u_z(x_0, 0, \omega)| \left( \sqrt{\frac{\pi x_0 + \left(\frac{\omega}{c}\right)\sigma_y^2}{\pi x_1 + \left(\frac{\omega}{c}\right)\sigma_y^2}} \right), \quad \text{[Equation 5]}$$

That is, the attenuation coefficient and the attenuation coefficient dispersion may be calculated by calculating the attenuation of the wave after correcting the observed waveform using [Equation 5].

On the other hand, the velocity c of the shear wave used in [Equation 5] may be calculated from the change depending on the observed displacement or the position of the particle velocity, by various methods such as solving the wave equation, calculating the correlation coefficient (auto correlation), or peak tracking for tracking the peak value.

Hereinafter, another method for calculating the velocity c of the shear wave will be described.

The kinetic energy K (x, t) of the wave is proportional to the square of the velocity, and thus may be defined by [Equation 6].

$$K(x,t)=[v_z(x,t)]^2 \quad \text{[Equation 6]}$$

The total energy at position x is calculated as [Equation 7] by Parseval's theory.

$$K(x) = \int_0^\infty [v_z(x, t)]^2 dt = \int_0^\infty \text{Re}[v_z(x, 0, \omega)]^2 d\omega. \quad \text{[Equation 7]}$$

Since the velocity of the wave may eventually be defined as the velocity at which the energy of the wave travels with time, the velocity of the shear wave may be acquired by calculating the center time at each position x and calculating its slope. At this time, the center time is the first momentum of the kinetic energy and may be calculated as [Equation 8].

$$\overline{t_x} = \frac{\int_0^\infty t \cdot K(x, t) dt}{\int_0^\infty K(x, t) dt} \quad \text{[Equation 8]}$$

The velocity of the shear wave may be calculated by [Equation 9].

$$c = \frac{\Delta x}{\Delta \overline{t_x}} \quad \text{[Equation 9]}$$

Where c is the velocity of the shear wave, $\Delta x$ is the amount of change in position, and $\Delta \overline{t_x}$ is the amount of change in the center time.

On the other hand, the dispersion of the parameter due to the viscosity also occurs at the velocity c of the shear wave and the attenuation coefficient $\alpha$, and thus may be expressed by [Equation 10] and [Equation 11] according to the frequency, respectively.

$$c = c_0 + c_1 |\omega| \quad \text{[Equation 10]}$$

$$\alpha = \alpha_0 + \alpha_1 |\omega| \quad \text{[Equation 11]}$$

Therefore, when the shear waves compensated for the geometric spreading are compared at positions $x_0$ and $x_1$, the damping effect may be expressed by [Equation 12].

$$\left|\frac{u'_d(x_1, \omega)}{u'_d(x_0, \omega)}\right| = e^{-\alpha_1|\omega|\Delta x}.$$  [Equation 12]

The position vector is defined by [Equation 13], and the frequency vector is defined by [Equation 14].

$$x = [x_1 \ldots x_m \ldots x_M]^T \in R^M$$  [Equation 13]

$$\omega = [\omega_1 \ldots \omega_n \ldots \omega_N]^T \in R^N$$  [Equation 14]

From these, the matrix of [Equation 15] is calculated as follows.

$$U_{mn} = -(\ln|u'_d(x_1,\omega)| - \ln|u_d(x_0,\omega)|).$$  [Equation 15]

At this time, the equation including the damping coefficient becomes the form of [Equation 16], and when [Equation 16] is solved by the least squares method, the damping coefficient may be finally calculated as shown in [Equation 17].

$$U_\alpha = \alpha_1 x \omega^T$$  [Equation 16]

$$\alpha = \frac{x^T U_\alpha \omega}{(x^T x)(\omega^T \omega)}.$$  [Equation 17]

Further, the velocity may be calculated by [Equation 18].

$$\frac{1}{c_0} = \frac{x^T U_c \omega}{(x^T x)(\omega^T \omega)} \Rightarrow c_0 = \frac{(x^T x)(\omega^T \omega)}{x^T U_c \omega}.$$  [Equation 18]

A physical error may occur in one or more of the viscoelastic parameters described above. It is helpful to present the reliability of the value to the user along with the value of each viscous parameter if measurement error is accompanied by various reasons such as the reflection of the shear wave and a patient's movement caused by breathing.

The error range, a ratio of the value of the interquartile range (IQR) to the median (MED) value, the standard deviation and the like are mainly used as the parameters indicating the reliability.

The user may perform a diagnosis of a specific disease by utilizing the displayed parameter value and the reliability thereof. However, since the viscoelasticity data has a large number of parameter values to be displayed as described above and parameters indicating reliability thereof are separately displayed, the user has the inconvenience of individually confirming the reliability of the displayed parameter values.

Further, since the user must perform a diagnosis of a specific disease by comparing the displayed reference data with the displayed viscoelasticity data by himself or herself, problems of inconvenience and misdiagnosis may occur.

Hereinafter, an ultrasound imaging apparatus capable of improving the convenience and accuracy of diagnosis in the method of displaying the viscoelasticity data will be described with reference to FIG. 2.

Figure 2:
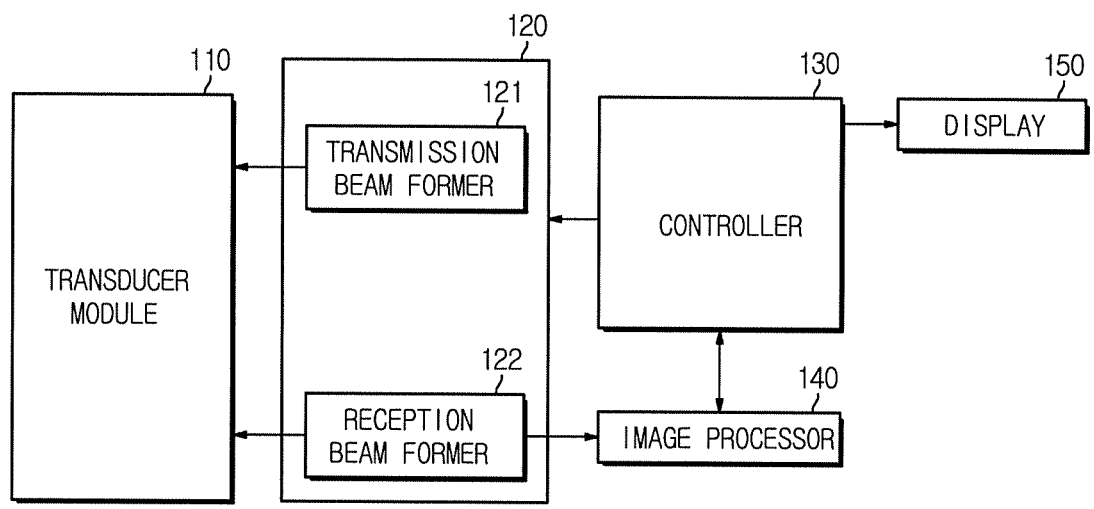
FIG. 2 is a control block diagram of an ultrasound imaging apparatus according to an embodiment.

FIG. 2 is a control block diagram of the ultrasound imaging apparatus according to an embodiment.

Referring to FIG. 2, the ultrasound imaging apparatus 100 according to an embodiment includes a transducer module 110 for converting an electric signal into an ultrasonic signal or an ultrasonic signal into an electric signal, a beam former 120 for generating a transmission beam and a reception beam, an image processor 140 for generating an ultrasound image using an echo signal output from the beam former 120, a controller 130 for controlling the operation of internal components of the ultrasound imaging apparatus 100, the display 150, and the inputter 170.

The transducer module 110 may convert an electric signal into an ultrasonic signal or an ultrasonic signal into an electric signal. To this end, the transducer module 110 may comprise an ultrasonic transducer of various elements, and the ultrasonic transducer may be implemented as any one of a piezoelectric ultrasonic transducer using a piezoelectric effect of a piezoelectric material, a magnetostrictive ultrasonic transducer using a magnetostrictive effect of a magnetic material, a capacitive micromachined ultrasonic transducer (cMUT) that transmits and receives ultrasonic waves by using vibrations of several hundreds or thousands of micromachined thin films, and the like. In addition, other types of transducers capable of generating ultrasonic waves in accordance with electrical signals or generating electrical signals in accordance with ultrasonic waves may also be examples of ultrasonic transducers.

Further, the transducer module 110 may further include a switch such as a multiplexer (MUX) for selecting a transducer element to be used for transmitting and receiving ultrasonic signals.

The transducer module 110 may be provided inside the ultrasonic probe P described above.

The beam former 120 may generate a transmission beam and a reception beam and may include a transmission beam former 121 and a reception beam former 122 for this purpose.

The transmission beam former 121 may perform transmission beamforming. The transmission beam former 121 may generate a transmission beam by applying a time delay to the ultrasonic signal transmitted from the transducer module 110.

The generated transmission beam may be transmitted through the transducer module 110, and the transmitted ultrasonic wave may be reflected on a target object and may be incident on the transducer module 110 again. As such, when the echo ultrasonic wave reflected from the target object is received, the transducer module 110 may output an echo signal corresponding to the received echo ultrasonic wave. The output echo signal is input to the reception beam former 122.

Further, the transmission beam former 121 may transmit a pushing pulse along an ultrasonic pushing line. The pushing pulse transmitted by the transmission beam former 121 may generate a shear wave to cause displacement of a tissue. Such a displacement of a tissue may be utilized as a control basis for measuring the velocity of the shear wave by the controller 130, which will be described later.

The reception beam former 122 may output echo signals with a predetermined time delay, and may synthesize the echo signals by applying a weight to each echo signal. In addition, the reception beam former 122 may amplify an echo signal and perform gain correction.

The image processor 140 may generate images of various modes based on an echo signal output from the reception beam former 122.

For example, the image processor 140 may generate at least one of an A-mode image, a B-mode image, a D-mode image, an E-mode image, and an M-mode image based on an echo signal. In addition, the image processor 140 may generate a 3D ultrasound image based on a plurality of ultrasound images acquired from an echo signal.

Further, the image processor 140 may perform image processing for representing various additional information on the ultrasound image.

To this end, the image processor 140 may be implemented in the form of hardware such as a microprocessor, or may be implemented in the form of software that may be executed on hardware.

The display 150 may display the generated ultrasound image and various data required for diagnosis. In addition, the display 150 may display the data acquired from the ultrasonic probe P in the ultrasound image in a map format in accordance with the control of the controller 130, which will be described later.

The controller 130 may control various configurations of the ultrasound imaging apparatus 100. The controller 130 may control the beam former 120 to generate a signal for acquiring viscoelasticity data for a target object and may control the image processor 140 to generate an ultrasound image.

The controller 130 may acquire the viscoelasticity data by measuring the displacement of the tissue caused by the pushing pulse transmitted by the transmission beam former 121 or the particle velocity.

The controller 130 may determine a parameter for displaying the viscoelasticity data of the target object and determine a parameter space for displaying the parameter.

The parameter space refers to a space for visually providing specific parameters and other information together, or for visually representing a relationship between two or more parameters.

The controller 130 determines a parameter for displaying the viscoelasticity data and a parameter space, and displays the viscoelasticity data of the target object in the determined parameter space, so that the user may easily observe the viscoelasticity data and intuitively grasp the meaning represented by the viscoelasticity data. In order to facilitate the user's intuitive understanding of the viscoelasticity data, the controller 130 may determine a two-dimensional coordinate space or a three-dimensional coordinate space as a parameter space for displaying the viscoelasticity data of the target object.

Further, the controller 130 may determine at least one parameter of the shear wave speed, the shear wave attenuation coefficient, the shear wave speed dispersion, the shear wave attenuation dispersion, the viscosity, and the shear modulus as a parameter for forming the above-described parameter space.

The controller 130 may display a region corresponding to a predetermined level in the determined parameter space. A detailed description thereto will be given later.

The acquired viscoelasticity data and the parameters determined therefrom are provided to the user in various forms, and specific embodiments will be described later.

The controller 130 may control the display 150 to display the ultrasound image generated by the image processor 140 and related parameters.

Figure 3:
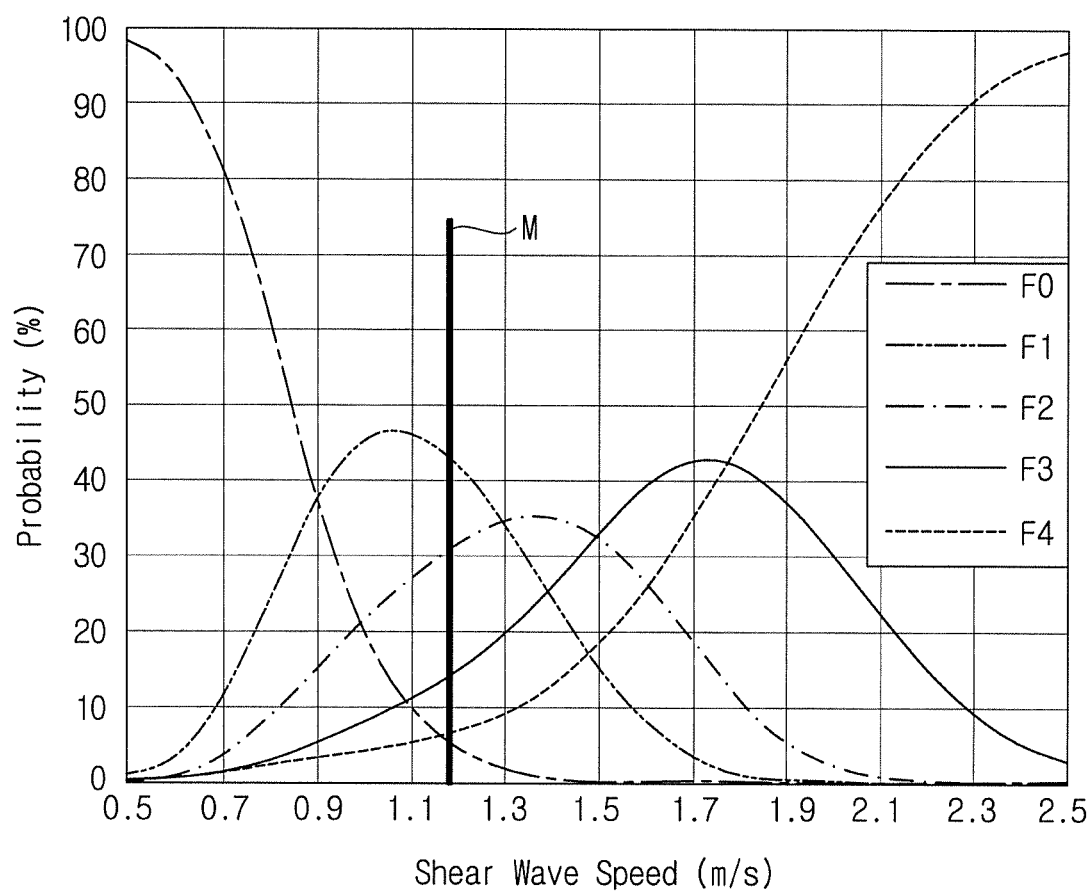
FIG. 3 is a view illustrating an example displayed on a screen of an ultrasound imaging apparatus according to an embodiment.

FIG. 3 is a view illustrating an example displayed on a screen of the ultrasound imaging apparatus according to an embodiment.

Referring to FIG. 3, the controller 130 according to an embodiment may determine the parameter displayed in a parameter space to be displayed on the display 150 as a shear wave speed.

The controller 130 may determine the liver fibrosis probability distribution space according to the shear wave speed as a parameter space to be displayed on the display 150.

The controller 130 may display the liver fibrosis probability by a liver fibrosis level in the liver fibrosis probability distribution space according to the shear wave speed, and the level of liver fibrosis may represent the development stage of liver fibrosis.

The controller 130 may display a region corresponding to each level in the liver fibrosis probability distribution space by distinguishing the liver fibrosis level into one or more levels.

For example, the controller 130 may distinguish the liver fibrosis level into the levels of F0, F1, F2, F3, and F4. Herein, the F0 level may be the case where the degree of liver fibrosis is from 2.0 kPa or more to less than 4.5 kPa, the F1 level may be the case where the degree of liver fibrosis is from 4.5 kPa or more to less than 5.7 kPa, the F2 level may be the case where the degree of liver fibrosis is from 5.7 kPa or more to less than 9.5 kPa, the F3 level may be the case where the degree of liver fibrosis is from 9.5 kPa or more to less than 12.4 kPa, and the F4 level may be the case where the degree of liver fibrosis is 12.4 kPa or more. The controller 130 may perform similarly to liver steatosis and inflammation level.

The controller 130 may display the liver fibrosis levels with lines, and may display various regions having different shapes to be distinguished from each other. For example, the controller 130 may display the regions corresponding to one or more levels with different colors or different shapes, and the display method is not limited to the example described above.

The controller 130 may display the acquired viscoelasticity data M in the liver fibrosis probability distribution space according to the shear wave speed in which a region corresponding to the liver fibrosis level distinguished by one or more levels is displayed.

In this case, the controller 130 may display the acquired viscoelasticity data M using a marker or color. In addition to that shown in FIG. 3, the controller 130 may represent the viscoelasticity data M in the form of a bar, an asterisk, a circle, and the like, but the present invention is not limited thereto.

The controller 130 may increase the utility of the user by displaying measured values in a medically useful and meaningful parameter space without simply displaying numbers. In addition, since in diagnosing a specific disease, the user may determine the stage for the specific disease without comparing the viscoelasticity data with separate criteria reference materials, the convenience and accuracy of diagnosis may be increased.

Figure 4:
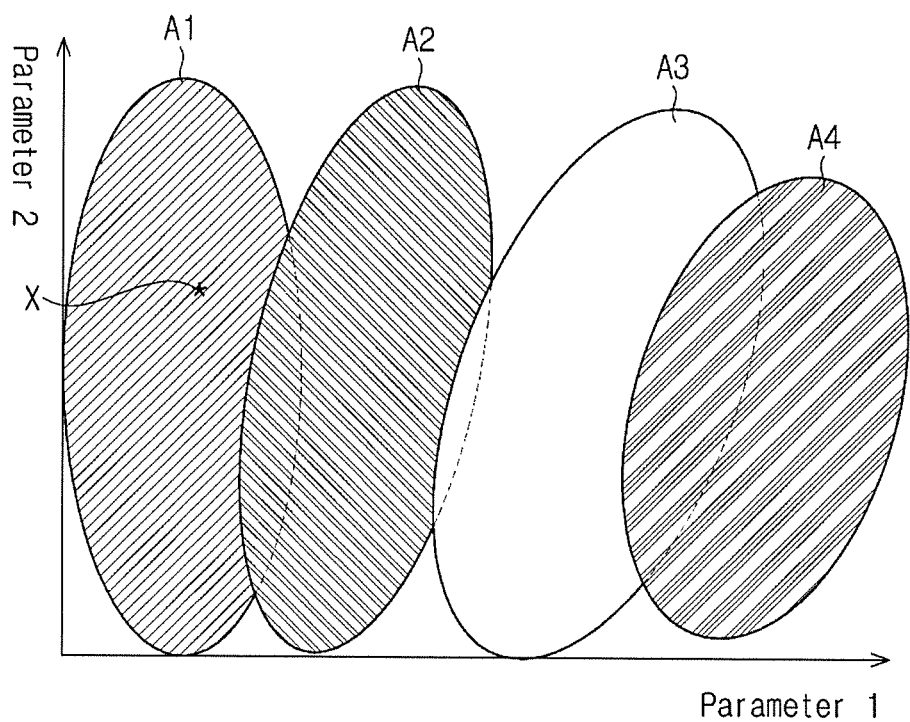
FIG. 4 is a view illustrating an example displayed on a screen of an ultrasound imaging apparatus according to an embodiment.

FIG. 4 is a view illustrating an example displayed on a screen of the ultrasound imaging apparatus according to an embodiment.

Referring to FIG. 4, the controller 130 according to an embodiment may determine the parameter space as a two-dimensional coordinate space and determine the x-axis parameter (parameter 1) and the y-axis parameter (parameter 2) constituting the two-dimensional coordinate space.

The controller 130 may display regions A1, A2, A3, and A4 corresponding to the predetermined levels in the parameter space. Each region is a space acquired by statistically processing integrated clinical data, and each region shown in FIG. 4 is intended to be conceptually explained.

Specifically, the controller 130 may partition the parameter space based on the parameter values corresponding to the predetermined levels for the determined parameters. The controller 130 may display the regions A1, A2, A3, and A4 for the level in the parameter space by associating the partitioned parameter space with the predetermined level.

The partition of the parameter space may be in many forms depending on the clinical application. For example, parameter 1 can be shear wave speed thereby denoting elasticity while parameter 2 can be shear wave attenuation or shear speed dispersion thereby denoting viscosity. In this scheme, level of liver fibrosis and liver steatosis (or inflammation) may be understood simultaneously.

For example, the controller 130 may display a region corresponding to liver fibrosis level. In addition, the controller 130 may display a region corresponding to a diagnostic level at which the viscoelasticity data of a tissue may be utilized, and is not limited to the example described above.

The controller 130 may display the regions A1, A2, A3, and A4 corresponding to the predetermined levels so that they may be distinguished from each other, and may display the regions using the marker, color, and character.

The controller 130 may display the regions corresponding to the predetermined levels, and at the same time display the viscoelasticity data X acquired from the target object.

Accordingly, since the user may intuitively determine to which region the acquired viscoelastic data belongs, convenience in diagnosing a specific disease of the object may be enhanced.

The difference between the embodiment of FIG. 3 and the embodiment of FIG. 4 is that the embodiment of FIG. 3 is a parameter space for one parameter and the embodiment of FIG. 4 is a parameter space for two parameters. The controller 130 may determine one or more parameters to constitute the parameter space, and the number of parameters that constitute the parameter space is not limited to the example described above.

Figure 5:
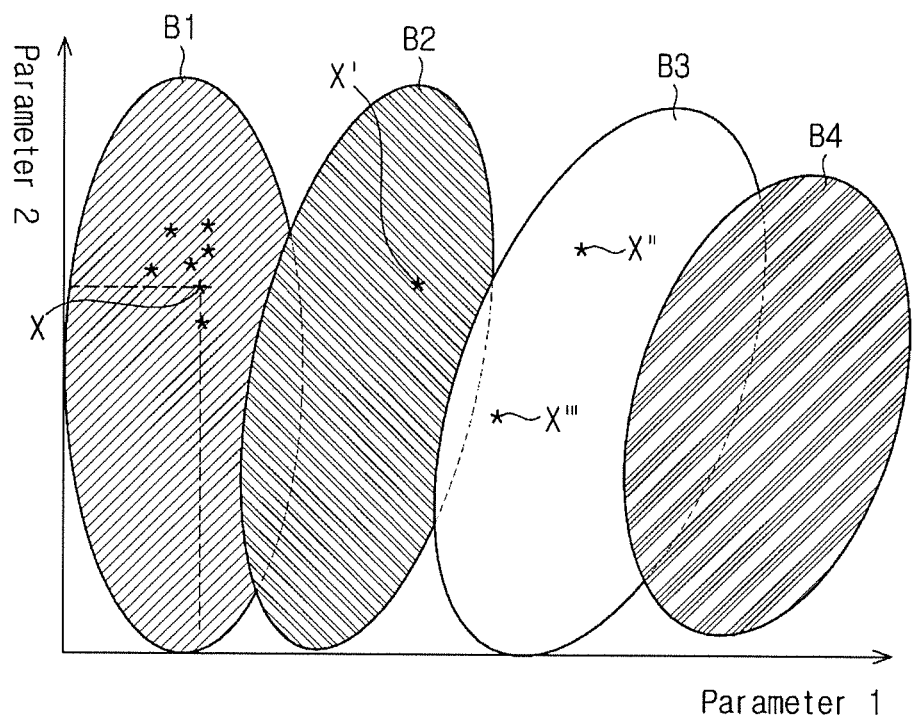
FIG. 5 is a view illustrating an example displayed on a screen of an ultrasound imaging apparatus according to an embodiment.

FIG. 5 is a view illustrating an example displayed on a screen of the ultrasound imaging apparatus according to an embodiment.

Referring to FIG. 5, the controller 130 according to an embodiment may generate a predetermined number of image frames based on the generated ultrasound images and may display viscoelasticity data for the generated predetermined number of image frames.

The controller 130 may display viscoelasticity data X, X', X", and X''' measured several times together with regions B1, B2, B3 and B4 corresponding to the predetermined levels, and the number of displayed viscoelasticity data items may be determined according to the number of generated image frames.

At this time, the user may confirm the distribution of the acquired viscoelasticity data, remove the low reliability data far away from the representative group, and select the representative group with high reliability and calculate the representative value X thereof.

As another example, the controller 130 may calculate an average value of at least one viscoelasticity data for the generated image frames, and may display the average value of the viscoelasticity data in the parameter space.

Through this, the user may intuitively confirm the distribution of the acquired viscoelasticity data and may exclude the data with relatively low reliability from the distribution of the data in diagnosing the target object. Therefore, the convenience and accuracy of diagnosis may be increased.

Figure 6A:
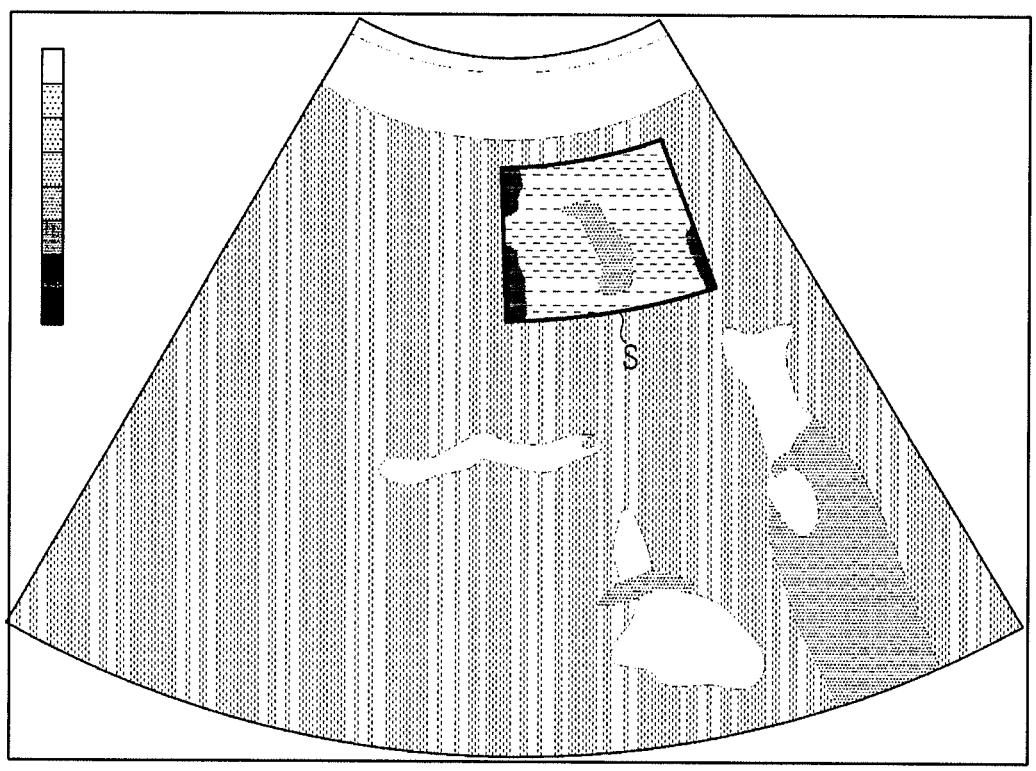
FIGS. 6a and 6b are views illustrating examples displayed on a screen of an ultrasound imaging apparatus according to an embodiment.
Figure 6B:
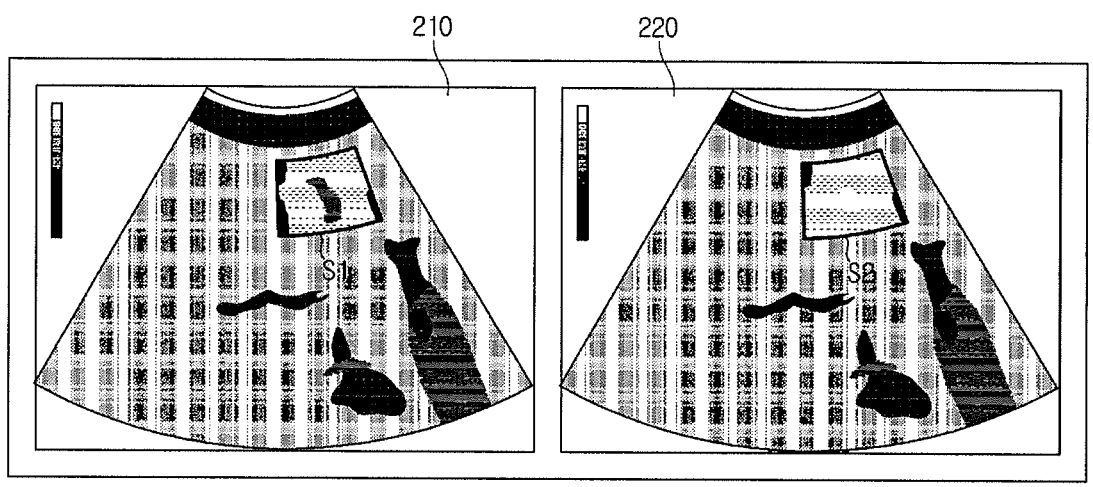

FIGS. 6a and 6b are views illustrating examples displayed on a screen of the ultrasound imaging apparatus according to an embodiment.

Referring to FIG. 6a, the controller 130 according to an embodiment may display the acquired viscoelasticity data in a generated ultrasound image in a map form.

Further, the controller 130 may display the average value of the acquired viscoelasticity data in an ultrasound image in a map form.

Specifically, the controller 130 may control the image processor 140 to generate a predetermined number of image frames, and may calculate an average value of the viscoelasticity data for the predetermined number of generated image frames.

The controller 130 may display the average value of the viscoelasticity data for the predetermined number of image frames in the form of a map in a region of interest S of the ultrasound image.

At this time, the region of interest S may be input from the user, and may be automatically set by the ultrasound imaging apparatus 100. The viscoelastic data in which the average value is displayed in the region of interest S in the form of a map means viscoelasticity data acquired for the region of interest S.

Accordingly, since the user may observe the average value of the viscoelasticity data without much regard to the reliability of the viscoelasticity data for the currently acquired image frame, the accuracy of diagnosis may be increased.

Referring to FIG. 6b, the controller 130 according to an embodiment may display the average value of the viscoelasticity data for the above-described predetermined number of image frames in a first region 210 in a map form, and may display the viscoelasticity data for the currently acquired image frame in a second region 220 in a map form.

At this time, the viscoelasticity data for the currently acquired image frame refers to viscoelasticity data for the most recently acquired image frame.

Accordingly, the user may easily visually compare the viscoelasticity data for the currently acquired image frame with the average value of the viscoelasticity data for a predetermined number of image frames. At the same time, the user may estimate the reliability of the viscoelasticity data for the currently acquired image frame, and thus the convenience of diagnosis may be increased.

Figure 7:
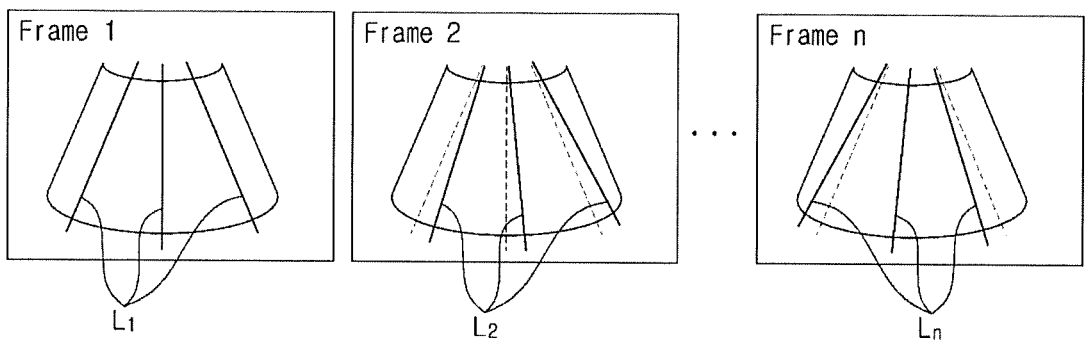
FIG. 7 is a view for explaining an operation of acquiring viscoelasticity data by an ultrasound imaging apparatus according to an embodiment.

FIG. 7 is a view for explaining an operation of the ultrasound imaging apparatus according to an embodiment to emit a pushing pulse in order to generate a shear wave.

In a normal viscoelasticity measurement system, it is common to use a fixed push beam. In this case, there is no big problem when the medium is very homogeneous, but an error may occur when the medium is inhomogenous. That is, when the medium is inhomogenous, various phenomena such as reflection, scattering, and diffraction may occur as the shear waves propagate from the initial occurrence point of the shear waves to the observation point. Due to these phenomena, various errors occur in the basic assumption of constant wave progress. Therefore, when observing the same part in several frames for a predetermined time, it is advantageous to change the position of the pushing pulse rather than use the same pushing pulse. The controller 130 according to an embodiment may change the position of the ultrasonic pushing line from which the transmission beam former 121 transmits the pushing pulse.

Specifically, the controller 130 may control the transmission beam former 121 to transmit a pushing pulse to the region of interest (ROI) along a first pushing line L1, and acquire the viscoelasticity data corresponding to the pushing pulse.

Thereafter, the controller 130 may control the transmission beam former 121 to transmit the pushing pulse to the ROI along a second pushing line L2, and acquire the viscoelasticity data corresponding to the pushing pulse. At this time, the second pushing line L2 is a pushing line indicating a position different from the first pushing line L1.

By repeating this process, the controller 130 may control the transmission beam former 121 to transmit the pushing pulse to the ROI along an nth pushing line Ln, and acquire the viscoelasticity data corresponding to the pushing pulse.

Collectively, the controller 130 may change the position of the pushing line until acquiring a predetermined number (n) of viscoelasticity data items for the regions of interest (ROIs).

In order to acquire viscoelasticity data of the predetermined number (n) for the ROIs, the controller 130 may control the transmission beam former 121 so that the positions of the pushing lines from which the pushing pulses are transmitted are different from each other.

Accordingly, the controller 130 may measure the viscoelasticity data for the region of interest (ROI) at various positions, and may reduce errors that may occur when measuring viscoelasticity data in a tissue, which is an inhomogeneous medium, using a pushing pulse. Therefore, since the accuracy of the acquired viscoelasticity data may be increased, a more accurate diagnosis of the target object may be made.

Figure 8:
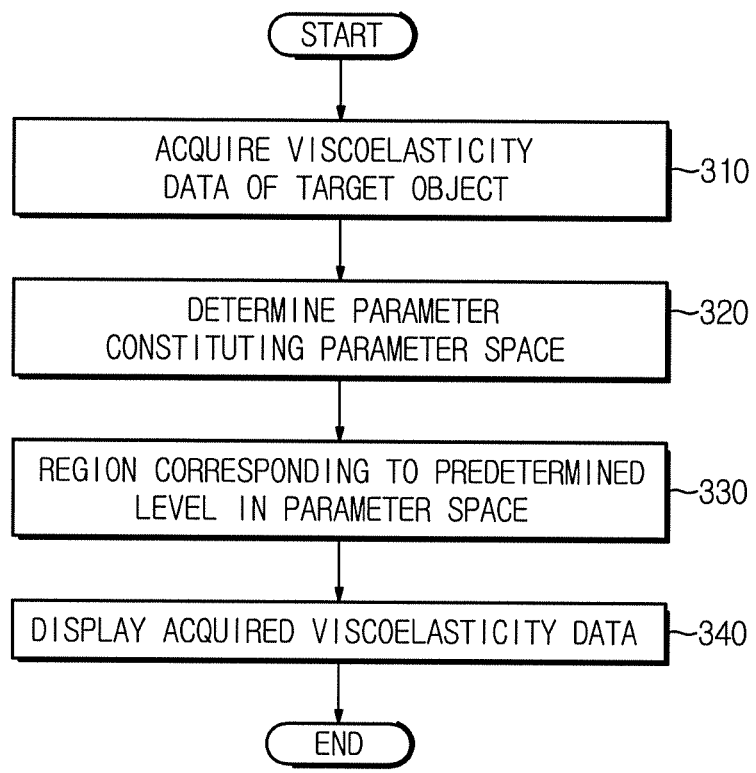
FIG. 8 is a flowchart illustrating a control method of an ultrasound imaging apparatus according to an embodiment.

FIG. 8 is a flowchart illustrating a control method of the ultrasound imaging apparatus according to an embodiment.

Referring to FIG. 8, the ultrasound imaging apparatus 100 according to an embodiment may acquire viscoelasticity data of a target object (310).

Specifically, the ultrasound imaging apparatus 100 may generate a shear wave by transmitting a pushing pulse along an ultrasonic pushing line, and acquire the viscoelasticity data of the tissue of the target object by measuring the property of the generated shear wave.

The ultrasound imaging apparatus 100 may determine a parameter that constitutes a parameter space for displaying the acquired viscoelasticity data (320).

In this case, the parameter space may refer to a two-dimensional coordinate space or a three-dimensional coordinate space. In addition, the ultrasound imaging apparatus 100 may determine parameters for determining the axes of the parameter space to be at least one of the shear wave speed, the shear wave attenuation coefficient, the shear wave speed dispersion, the shear wave attenuation dispersion, the viscosity, and the shear modulus.

When the parameters to constitute the parameter space are determined, the ultrasound imaging apparatus 100 may display regions corresponding to a predetermined level in the parameter space (330).

Specifically, the ultrasound imaging apparatus 100 may partition the parameter space based on the parameter value corresponding to the predetermined level for the determined parameter. The ultrasound imaging apparatus 100 may display a region for the level in the parameter space by associating the partitioned parameter space with the predetermined level.

In this case, the predetermined level may be a plurality of levels, and the ultrasound imaging apparatus 100 may display the levels using the marker, color, and character so that the regions corresponding to the predetermined levels may be distinguished from each other.

Thereafter, the ultrasound imaging apparatus 100 may display the acquired viscoelasticity data (340). The ultrasonic imaging apparatus 100 may display the region corresponding to the predetermined level, and at the same time display the viscoelasticity data acquired from the target object.

Accordingly, the ultrasound imaging apparatus 100 may allow the user to intuitively determine to which region the acquired viscoelasticity data belongs. Therefore, the convenience of diagnosis of a specific disease for a target object may be increased.

Figure 9:
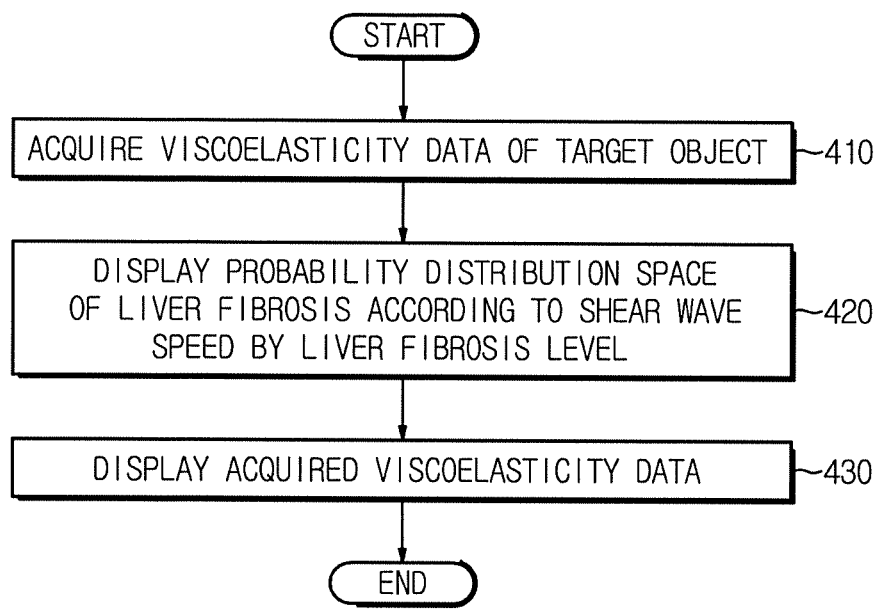
FIG. 9 is a flowchart illustrating a control method of an ultrasound imaging apparatus according to an embodiment.

FIG. 9 is a flowchart illustrating a control method of the ultrasound imaging apparatus according to an embodiment.

Referring to FIG. 9, the ultrasound imaging apparatus 100 according to an embodiment may acquire viscoelasticity data of a target object (410).

When the viscoelasticity data for the target object is acquired, the ultrasound imaging apparatus 100 may display the probability distribution space of liver disease according to the viscoelastic properties measured through shear wave by the level of liver disease (420). In this case, the level of liver disease may represent the development stage of liver disease.

Specifically, the ultrasound imaging apparatus 100 may display a region corresponding to each level in the liver fibrosis probability distribution space by distinguishing the liver fibrosis level into one or more levels.

Further, the ultrasound imaging apparatus 100 may display the regions corresponding to one or more liver fibrosis levels with different colors or different shapes, and the display method is not limited thereto.

Thereafter, the ultrasound imaging apparatus 100 may display the acquired viscoelasticity data (430). Specifically, the ultrasound imaging apparatus 100 may display the acquired viscoelasticity data in the liver fibrosis probability distribution space according to the shear wave speed in which a region corresponding to the liver fibrosis level distinguished by one or more levels is displayed.

In this case, the ultrasound imaging apparatus 100 may display the acquired viscoelasticity data M using the marker or color, and may represent the viscoelasticity data in the form of a bar, an asterisk, a circle, and the like.

Accordingly, since the user may determine the development stage for the liver fibrosis without comparing the viscoelasticity data with separate reference materials, the convenience and accuracy of diagnosis may be increased.

Figure 10:
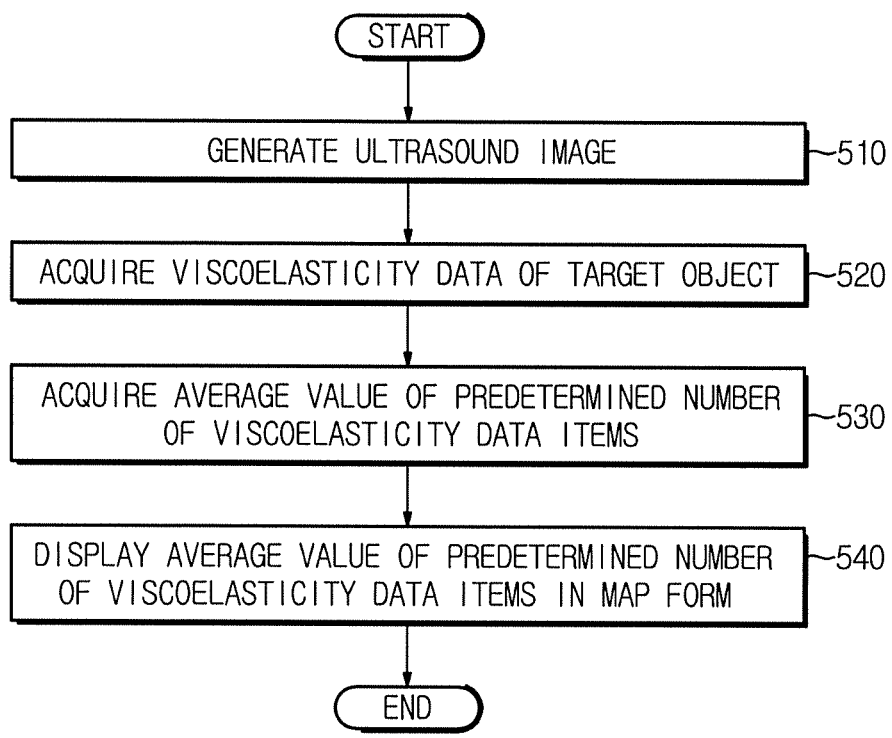
FIG. 10 is a flowchart illustrating a control method of an ultrasound imaging apparatus according to an embodiment.

FIG. 10 is a flowchart illustrating a control method of the ultrasound imaging apparatus according to an embodiment.

Referring to FIG. 10, the ultrasound imaging apparatus 100 according to an embodiment may generate an ultrasound image (510) and acquire viscoelasticity data of the target object (520).

Specifically, the ultrasound imaging apparatus 100 may generate an ultrasound image by generating an image frame, and acquire the resulting viscoelasticity data. In this case, the ultrasound imaging apparatus 100 may generate a predetermined number of image frames, and acquire the viscoelasticity data for the predetermined number of generated image frames.

In FIG. 10, steps 510 and 520 are shown to be performed sequentially, but the present disclosure is not limited thereto. That is, the steps may be performed simultaneously or the order may be reversed.

Thereafter, the ultrasound imaging apparatus 100 may acquire an average value of the predetermined number of viscoelasticity data items (530), and may display the average value of the predetermined number of viscoelasticity data items in a map form (540).

At this time, the ultrasound imaging apparatus 100 may display the average value of the predetermined number of viscoelasticity data in a map form on the generated ultrasound images, and on an image corresponding to a region of interest among the ultrasound images in a map form.

Accordingly, since the user may observe the average value of the viscoelasticity data without being significantly affected by the reliability of the viscoelasticity data for the currently acquired image frame, the accuracy of diagnosis may be increased.

FIG. 11 is a flowchart illustrating a control method of the ultrasound imaging apparatus according to an embodiment.

Referring to FIG. 11, the ultrasound imaging apparatus 100 according to an embodiment may confirm whether a region of interest (ROI) is set or not (610). In this case, the region of interest (ROI) may be input from the user or automatically set by the ultrasound imaging apparatus 100.

When the ROI is set (YES in 610), the ultrasound imaging apparatus 100 may transmit a push beam to the ROI along the pushing line (620). The push beam refers to a transmission beam capable of generating a shear wave, and may include a pushing pulse transmitted by the transmission beam former 121.

By measuring the property of the shear wave caused by the push beam transmitted to the region of interest along the pushing line, the ultrasound imaging apparatus 100 may acquire the viscoelasticity data (630).

When the viscoelasticity data is acquired, the ultrasound imaging apparatus 100 may change the pushing line of the region of interest (640). Specifically, the ultrasound imaging apparatus 100 may change the pushing line of the region of interest by setting the pushing line to a position different from the position where the viscoelasticity data is acquired.

Thereafter, the ultrasound imaging apparatus 100 may transmit the push beam to the region of interest along the changed pushing line (650), and acquire the viscoelasticity data therefor (660).

The ultrasound imaging apparatus 100 may confirm whether the number of the acquired viscoelasticity data items has a value larger than the predetermined number (670).

If the number of acquired viscoelasticity data items is smaller than or equal to the predetermined number (NO in 670), the ultrasound imaging apparatus 100 may change the pushing line and transmit the push beam to the region of interest along the changed pushing line to acquire the viscoelasticity data. That is, steps 640 to 660 may be repeated.

If the number of acquired viscoelasticity data items is larger than the predetermined number (NO in 670), the ultrasound imaging apparatus 100 may display an average value of the acquired viscoelasticity data in a map form (680).

Specifically, the ultrasound imaging apparatus 100 may calculate an average value of the acquired viscoelasticity data, and display the average value of the calculated viscoelasticity data on the ultrasound image in a map form.

Accordingly, the ultrasound imaging apparatus 100 may measure the viscoelasticity data for the region of interest (ROI) at various positions, and may reduce errors that may occur when measuring viscoelasticity data in a tissue, which is an inhomogeneous medium, using a pushing pulse. Therefore, since the accuracy of the acquired viscoelasticity data may be increased, a more accurate diagnosis of the target object may be made.

As is apparent from the above, according to the ultrasonic imaging apparatus and the control method thereof according to one aspect of the present disclosure, the convenience and accuracy of diagnosis can be improved by determining the parameter space in which the viscoelasticity data is displayed. At the same time, the reliability of the data can be increased by measuring the viscoelastic data at various positions.

Although a few embodiments of the present disclosure have been shown and described, it would be appreciated by those skilled in the art that changes may be made in these embodiments without departing from the principles and spirit of the disclosure, the scope of which is defined in the claims and their equivalents. The disclosed embodiments are illustrative and should not be construed as limiting.

What is claimed is:

1. An ultrasound imaging apparatus comprising:
an ultrasonic probe to acquire an ultrasonic signal of a target object;
a display; and
a controller configured
to acquire viscoelasticity data of the target object based on the acquired ultrasonic signal;
to determine at least two parameters derived from the viscoelasticity data for displaying the viscoelasticity data;
to determine a parameter space for displaying the at least two parameters;
to generate regions corresponding to levels of liver disease based on correlation of the at least two parameters,
wherein each of the regions comprises a plurality of viscoelasticity data points;
to generate a marking on at least one of the plurality of viscoelasticity data points to distinguish the regions that corresponds to predetermined levels of liver disease from each other; and
to control the display to display the at least two parameters in the parameter space, the regions in the parameter space, and the marking,
wherein the at least two parameters are displayed simultaneously, and
wherein the levels of liver disease are determined according to development of the liver disease.

2. The ultrasound imaging apparatus according to claim 1, wherein the parameter space is a two-dimensional coordinate space or a three-dimensional coordinate space.

3. The ultrasound imaging apparatus according to claim 1, wherein the at least two parameters for displaying the viscoelasticity data are at least two of a shear wave speed, a shear wave attenuation coefficient, a shear wave speed dispersion, a shear wave attenuation dispersion, a viscosity, and a shear modulus.

4. The ultrasound imaging apparatus according to claim 1, wherein liver diseases include fibrosis, steatosis or inflammation.

5. The ultrasound imaging apparatus according to claim 1, wherein the controller determines a liver disease probability distribution space as the parameter space, and controls the display to display a liver disease probability distribution and the viscoelasticity data for the level of the liver disease in the determined parameter space.

6. A control method of an ultrasound imaging apparatus, the method comprising:
acquiring an ultrasonic signal of a target object;
acquiring viscoelasticity data of the target object based on the acquired ultrasonic signal;
determining at least two parameters derived from the viscoelasticity data for displaying the viscoelasticity data;
determining a parameter space for displaying the at least two parameters;

generating regions corresponding to levels of liver disease based on correlation of the at least two parameters, wherein each of the regions comprises a plurality of viscoelasticity data points;

generating a marking on at least one of the plurality of viscoelasticity data points to distinguish the regions that corresponds to predetermined levels of liver disease from each other; and displaying the at least two parameters in the parameter space, the regions in the parameter space, and the marking, wherein the at least two parameters are displayed simultaneously, and wherein the levels of liver disease are determined according to development of the liver disease.

7. The control method according to claim 6, wherein the parameter space is a two-dimensional coordinate space or a three-dimensional coordinate space.

8. The control method according to claim 6, wherein the at least two parameters for displaying the viscoelasticity data are at least two of a shear wave speed, a shear wave attenuation coefficient, a shear wave speed dispersion, a shear wave attenuation dispersion, a viscosity, and a shear modulus.

9. The control method according to claim 6, wherein the step of determining the parameter space comprises determining a liver disease probability distribution space as the parameter space, and the step of displaying the determined parameter in the determined parameter space comprises displaying a liver disease probability distribution and the viscoelasticity data for the lever of the liver disease in the determined parameter space.

* * * * *